United States Patent [19]
Prakash et al.

[11] Patent Number: 5,977,415
[45] Date of Patent: Nov. 2, 1999

[54] PREPARATION OF 3,3-DIMETHYLBUTYRALDEHYDE FROM A TERT-BUTYL CATION PRECURSOR, VINYL CHLORIDE AND AN ACIDIC CATALYST

[75] Inventors: Indra Prakash, Hoffman Estates; Zhi Guo, Chicago, both of Ill.

[73] Assignee: The NutraSweet Company, Chicago, Ill.

[21] Appl. No.: 09/136,974

[22] Filed: Aug. 20, 1998

[51] Int. Cl.$^6$ ..................................................... C07C 45/50
[52] U.S. Cl. ........................... 568/490; 568/449; 568/488
[58] Field of Search ..................... 568/450, 427, 568/449, 488, 490; 426/548

[56] References Cited

U.S. PATENT DOCUMENTS

| | | | |
|---|---|---|---|
| 5,480,668 | 1/1996 | Nofre | 426/548 |
| 5,510,508 | 4/1996 | Claude | 560/41 |
| 5,728,862 | 3/1998 | Prakash | 560/40 |

FOREIGN PATENT DOCUMENTS

| | | |
|---|---|---|
| 1051551 | 5/1991 | China . |
| 2-006429 | 1/1990 | Japan . |
| 693390 | 7/1953 | United Kingdom . |

OTHER PUBLICATIONS

Bott, Angew.Chem., International Edition (English), vol. 19, pp. 171–178, 1980.

March, Advanced Organic Chemistry, third edition, pp. 142–143, 146, 150, 1985.

K. Bott, "Synthese Von 1–Adamantyl–acetaldehyden Und Homoadamantan–4–onen Aus Acetylen", Tetrahedron Lett., No. 22, pp. 1747–1749 (1969).

K. Bott,"Erzeugung und Reaktionen von 1–Adamantyl–vinyl–Kationen", Liebigs Ann. Chem., vol. 766, pp. 51–57 (1972).

K. Bott, "Tscherniac–Einhorn–Synthesen mit Chlorolefin und Acetylen", Chem. Ber., vol. 106, pp. 2513–2522 (1973).

K. Bott, "Aldehydsynthesen Mit 1,2–Dichlorathylen und Vinylchlorid", Tetrahedron Lett., No. 49, pp. 4301–4304 (1970).

*Primary Examiner*—Shailendra Kumar
*Assistant Examiner*—Sreeni Padmanabhan
*Attorney, Agent, or Firm*—Fitzpatrick, Cella, Harper & Scinto

[57] ABSTRACT

This invention provides a method for preparing 3,3-dimethylbutyraldehyde from a tert-butyl cation precursor and vinyl chloride. The tert-butyl cation precursor is contacted with vinyl chloride in the presence of an inorganic acid, and the product is allowed to react with water to form 3,3-dimethylbutyraldehyde.

4 Claims, No Drawings

PREPARATION OF 3,3-DIMETHYLBUTYRALDEHYDE FROM A TERT-BUTYL CATION PRECURSOR, VINYL CHLORIDE AND AN ACIDIC CATALYST

BACKGROUND OF THE INVENTION

1. Field of the Invention

This invention relates to a method for preparing 3,3-dimethylbutyraldehyde from a tert-butyl cation precursor, vinyl halides or acetylene, and an inorganic acid.

2. Related Background Art

Reactions of carbocation precursors, e.g., alkenes or alcohols, with alkenes, haloalkenes, or acetylene in the presence of an inorganic acid are well known, as reviewed by K. Bott, Angew. Chem., International Ed. (English), Vol. 19, pgs. 171–178.

The reaction of isobutylene with ethylene and sulfuric acid, followed by hydrolysis is known to produce 3,3-dimethylbutanol, as disclosed in British Patent No. 693,390.

Japanese Patent JP 02-006429 discloses the reaction of isobutylene with vinylidene dichloride and sulfuric acid, followed by hydrolysis to produce 3,3-dimethylbutyric acid.

Reactions of 1-adamantanol and its bridgehead derivatives with acetylene in sulfuric acid to generate aldehydes are disclosed by L. Bott in Tetrahedron Lett. (1969), pg. 1747, and Justus Liebigs Ann. Chem. Vol. 766 (1972), pg. 766.

Reaction of N-(hydroxymethyl)phthalimide with vinyl chloride in the presence of concentrated sulfuric acid to generate an aldehyde is disclosed in K. Bott, Tetrahedron Letters, (1970), pages 4301–04; K. Bott, Chemische Berichte, Vol. 106, pages 2513–22 (1973); and K. Bott, Angewandte Chemie International Edition (English), Vol. 19, pages 171–178 (1980). However, no suggestion is made that 3,3-dimethylbutyraldehyde could be synthesized in this manner.

There is no suggestion to react a tert-butyl cation precursor, vinyl halides, or acetylene, and an inorganic acid followed by hydrolysis to produce 3,3-dimethylbutyraldehyde.

3,3-Dimethylbutyraldehyde is an intermediate that is useful in the preparation of the sweetener N-[N-(3,3-dimethylbutyl)-L-α-aspartyl]-L-phenylalanine disclosed in U.S. Pat. No. 5,480,668 and U.S. Pat. No. 5,510,508. Accordingly, a method for preparing that intermediate which is both economical and specific is highly desired.

SUMMARY OF THE INVENTION

This invention is directed to a method for preparing 3,3-dimethylbutyraldehyde from a tert-butyl cation precursor and vinyl halides or acetylene. The method comprises the steps of: (a) contacting a tert-butyl cation precursor with vinyl halides or acetylene in the presence of an inorganic acid for a time and at a temperature sufficient for substantially complete consumption of the tert-butyl cation precursor; and (b) contacting the product derived from step (a) with water for a time and at a temperature sufficient to produce 3,3-dimethylbutyraldehyde.

DETAILED DESCRIPTION OF THE INVENTION

In the method of this invention, a tert-butyl cation precursor is allowed to react with vinyl halides or acetylene in the presence of an inorganic acid, followed by hydrolysis, to produce 3,3-dimethylbutyraldehyde. A suitable tert-butyl cation precursor is any compound which is capable of producing tert-butyl cation in the presence of an inorganic acid. Suitable tert-butyl cation precursors include, but are not limited to, isobutylene, tert-butyl alcohol, tertbutyl esters, e.g., tert-butyl acetate, and tert-butyl halides.

An inorganic acid is employed as a reagent in the method of this invention to promote the reaction of a tert-butyl cation precursor with vinyl halides or acetylene. Suitable inorganic acids include sulfuric acid, fuming sulfuric acid, hydrochloric acid, phosphoric acid, and the like.

The tert-butyl cation precursor, vinyl halide (such as, for example, vinyl chloride) and an organic acid are typically contacted at a temperature in the range from about $-30°$ C. to about $20°$ C., preferably from about $-20°$ C. to about $0°$ C., and most preferably at about $-10°$ C. The reaction is allowed to proceed for a period of time in the range from about 10 minutes to about 600 minutes, preferably from about 30 minutes to about 300 minutes, and most preferably for about 60 minutes.

Reaction of the first-step product with water is typically carried out at a temperature in the range from about $-10°$ C. to about $20°$ C., preferably from about $-5°$ C. to about $10°$ C., and most preferably at about $0°$ C. The reaction is allowed to proceed for a period of time in the range from about 1 minutes to about 120 minutes, preferably from about 10 minutes to about 60 minutes, and most preferably for about 30 minutes.

The example which follows is intended to illustrate a preferred embodiment of the invention, and no limitation of the invention is implied.

EXAMPLE

Preparation of 3,3-Dimethylbutyraldehyde

A round-bottom flask is equipped with a magnetic agitator, an addition funnel, a thermometer, a gas inlet and a dry ice condenser connected to a cold trap. 160 ml of concentrated sulfuric acid is loaded into the flask and cooled to $-5°$ C. 50 g tert-butyl acetate is added dropwise via the addition funnel with vigorous agitation. After this addition is complete, gaseous vinyl chloride is passed through the reaction mixture until no significant amount of gas uptake is observed. The mixture is stirred for an additional 60 minutes at $-5°$ C., then quenched by pouring it into ice. The organic layer is separated, washed with 1 N $Na_2CO_3$, dried with magnesium sulfate, and distilled to yield 3,3-dimethylbutyraldehyde.

Other variations and modifications of this invention will be obvious to those skilled in the art. This invention is not limited except as set forth in the claims.

What is claimed is:

1. A method for preparing 3,3-dimethylbutyraldehyde comprising the steps of:
   (a) contacting a tert-butyl cation precursor and vinyl chloride in the presence of an inorganic acid for a time and at a temperature sufficient for substantially complete consumption of the tert-butyl cation precursor; and
   (b) contacting a product of step (a) with water for a time and at a temperature sufficient to produce said 3,3-dimethylbutyraldehyde.

2. The method of claim 1, wherein the tert-butyl cation precursor is selected from the group consisting of isobutylene, tert-butyl alcohol, tert-butyl esters and tert-butyl halides.

3. The method of claim 2, wherein the inorganic acid is sulfuric acid, hydrochloric acid, phosphoric acid, or fuming sulfuric acid.

4. The method of claim 3, wherein the inorganic acid is sulfuric acid.

* * * * *